United States Patent [19]

Cikut et al.

[11] Patent Number: 5,118,871
[45] Date of Patent: Jun. 2, 1992

[54] MINIMIZING DEACTIVATION OF ETHER SYNTHESIS CATALYST

[75] Inventors: John J. Cikut, Kingwood, Tex.; Robert C. Michaelson, Kinnelon, N.J.; Dan E. Hendriksen, Kingwood, Tex.; Terry A. Fons, Baton Rouge, La.; Di-Yi Ou; Daniel D. Rosenfeld, both of Houston, Tex.

[73] Assignee: Exxon Chemical Patents Inc, Linden, N.J.

[21] Appl. No.: 645,352

[22] Filed: Jan. 24, 1991

Related U.S. Application Data

[63] Continuation of Ser. No. 274,557, Nov. 22, 1988, abandoned.

[51] Int. Cl.⁵ .............................................. C07C 41/06
[52] U.S. Cl. ..................................... 568/697; 568/699
[58] Field of Search ............................... 568/697, 699

[56] References Cited

U.S. PATENT DOCUMENTS

| | | |
|---|---|---|
| 3,306,945 | 3/1964 | Conviser . |
| 3,367,862 | 10/1965 | Mason et al. . |
| 3,629,478 | 12/1971 | Haunschild . |
| 3,634,534 | 1/1972 | Haunschild . |
| 3,726,942 | 4/1973 | Louder . |
| 3,846,008 | 11/1974 | Sobajima et al. . |
| 4,071,567 | 1/1978 | Ancillotti et al. . |
| 4,098,684 | 7/1978 | Innes . |
| 4,215,001 | 7/1980 | Elphingstone et al. . |
| 4,232,177 | 11/1980 | Smith, Jr. . |
| 4,242,530 | 12/1980 | Smith, Jr. . |
| 4,250,052 | 2/1981 | Smith, Jr. . |
| 4,254,296 | 3/1981 | Manara et al. . |
| 4,302,356 | 11/1981 | Smith, Jr. . |
| 4,307,254 | 12/1981 | Smith, Jr. . |
| 4,336,407 | 6/1982 | Smith, Jr. . |
| 4,375,576 | 3/1983 | Smith, Jr. . |
| 4,447,668 | 5/1984 | Smith, Jr. et al. . |
| 4,475,005 | 10/1984 | Paret . |
| 4,592,829 | 6/1986 | Eberly . |
| 4,831,206 | 5/1989 | Zarchy . |
| 4,831,207 | 5/1989 | O'Keefe et al. . |

*Primary Examiner*—Howard T. Mars
*Attorney, Agent, or Firm*—Edward F. Sherer

[57] ABSTRACT

A method for producing alkyl tertiary alkyl ether involves supplying a feed including isoolefins, alcohols, and dialkyl sulfides into a feed zone of a reactor; contacting the feed with a catalyst material in the reaction zone; and catalytically reacting the isooolefins and alcohols under conditions which favor forming resultant ether and inhibiting reaction of dialkyl sulfides with the catalyst material.

24 Claims, 2 Drawing Sheets

MINIMIZING DEACTIVATION OF ETHER SYNTHESIS CATALYST

This application is a continuation of application Ser. No. 07/274,557 filed Nov. 22, 1988 now abandoned.

BACKGROUND OF THE INVENTION

1. Field of the Invention

The present invention relates to methods of conducting catalytic chemical reactions under conditions so as to minimize or substantially avoid deactivation of the catalyst material due to a reaction of dialkyl sulfides with the catalyst material. More particularly, the present invention relates to the preparation of alkyl tertiary alkyl ether by catalytic reaction of hydrocarbon streams containing mixtures of isoolefins and alcohols under conditions which minimize or substantially avoid reaction of the catalytic material in the catalytic reaction zone with any dialkyl sulfides which may be present in the stream. Specifically, the present invention is directed to a catalytic reaction for producing alkyl tertiary alkyl ether which involves removing dialkyl sulfides from the hydrocarbon stream prior to introduction of the stream into the catalytic reaction zone and/or introducing sufficient amounts of oxygenates to the reaction zone to inhibit reaction of dialkyl sulfides which may be present in the stream with the catalyst material.

2. Discussion of Background and Material Information

Methyl tertiary butyl ether (MTBE) in recent years has become an important product of the petroleum industry in view of its acceptance as a non-environmentally harmful octane improver for gasolines.

In view of the octane improving characteristics of MTBE, processes, such as those disclosed in U.S. Pat. Nos. 3,726,942 and 3,846,008, have been developed to separate isoolefins, and isobutene in particular, from mixtures with corresponding normal olefins and alkanes which involves etherifying the isoolefins with a $C_1$ to $C_6$ primary alcohol in the presence of an acidic cation exchange resin catalyst followed by fractionation to separate the low boiling hydrocarbons from the higher boiling ether.

In a variation of these processes, as described in U.S. Pat. Nos. 3,629,478 and 3,634,534, HAUNSCHILD, the mixture of isoolefin and normal olefin with lower primary alcohols is fed to a distillation column in which there are a plurality of zones of acidic ion exchanges resin catalysts whereby the isoolefin ether is formed and drops to the bottom of the column while normal olefins, and paraffins, are distilled overhead.

More recently, catalytic distillation processes, such as those disclosed in U.S. Pat. Nos. 4,232,177, 4,307,254, and 4,336,407, SMITH, Jr., have been developed to improve the recovery of MTBE.

For example, U.S. Pat. No. 4,232,177, SMITH, Jr., is broadly directed to a method for concurrently conducting chemical reactions to produce a reaction mixture and fractionation of the reaction mixture which involves feeding reactants to a distillation column reactor into a feed zone. The reactants are then contacted with a fixed bed catalyst packing in a distillation-reaction zone, thereby catalytically reacting the reactants to form a reactant mixture. The reactant mixture is then fractionated in the fixed bed catalyst to recover a lower boiling fraction of the reaction mixture overhead and a higher boiling fraction as a bottom, whereby the reaction and fractionation occur concurrently in the fixed catalyst bed which serves as both catalyst and distillation packing in the distillation column reactor. It is disclosed that this method is particularly suitable for producing methyl tertiary butyl ether wherein the reactants include isobutene and methanol which is disclosed as preferably being present in a stoichiometric amount, although it is speculated that an excess of up to 10% of stoichiometric may be desirable.

U.S. Pat. No. 4,447,668, SMITH, Jr., is directed to disassociation of alkyl tertiary butyl ethers by vapor phase contact with a cation acidic exchange resin to produce a stream consisting of unreacted ether, isobutene, and an alcohol corresponding to the alkyl radicals.

U.S. Pat. Nos. 4,215,001 and 4,250,052, SMITH, Jr., are directed to a catalyst system and a catalyst structure, respectively, for separating isobutene from $C_4$ stream, respectively.

U.S. Pat. No. 4,375,576, SMITH, Jr., is directed to a liquid phase reaction of isobutene in the presence of resin cation exchange resins.

U.S. Pat. No. 4,242,530, SMITH, Jr., is directed to a method for the separation of isobutene from a mixture of n-butene and isobutene which involves feeding a $C_4$ stream containing isobutene to a distillation column reactor into a feed zone, contacting the stream with fixed bed acidic cation exchange resin to form diisobutene which passes to the bottom of the column and is removed.

U.S. Pat. No. 4,302,356, SMITH, Jr., is directed to a catalyst system for use in a reaction-distillation column which is a cloth belt having a plurality of pockets containing acid cation exchange resin arranged and supported by wire mesh intimately associated with the cloth pockets, particularly by pulling the cloth belt with the wire mesh disposed between the coils, i.e., in a spiral.

U.S. Pat. No. 4,071,567, ANCILLOTTI et al., is directed to a process for preparing methyl tert-butyl ether by reacting methanol with isobutene in the presence of an acid ion exchange resin in two stages by feeding the methanol and isobutene mixed with other hydrocarbons to respective members of a pair of interconnecting reactors so that the quantity of alcohol present in one of the reactors is in excess of the stoichiometric equivalent of the quantity of isobutene therein, while the quantity of isobutene present in the other reactor is in excess of the stoichiometric equivalent of the quantity of methanol therein, and the methyl tert-butyl ether so formed is recovered through distillation.

U.S. Pat. No. 4,254,296, MANARA et al., is directed to a process for preparing tertiary olefins from tertiary alkyl ethers, such as methyl tert-butyl ether which involves using a catalyst system which consists of a crystalline silica having a high specific surface area and which has been modified by an oxide of a metallic cation having at least partially amphoteric character.

U.S. Pat. No. 4,475,005, PARET, is directed to a process for preparing tertiary alkyl ethers from isoolefins and aliphatic alcohols in the presence of a catalyst characterized in that the reaction leading to the formation of the tert-alkyl ether and the separation of the tert-alkyl ether from the hydrocarbons and compounds which accompany it takes place in a single plate fractionating apparatus.

Notwithstanding the recent attempts to improve the production of isobutene and MTBE, a problem associated with conventional processes for the production of MTBE is that the catalyst material used in the catalyst reaction processes has a tendency to deactivate in an unacceptably short period of time.

SUMMARY OF THE INVENTION

The present invention is the discovery that dialkyl sulfides, such as dimethyl sulfide, if present in hydrocarbon streams, react with acidic sites on catalyst material so as to result in the neutralization of these sites with the concomitant loss of catalyst activity.

An object of the present invention, therefore, is the provision of methods for conducting catalytic reaction processes wherein the components of the hydrocarbon stream are catalytically reacted under conditions which favor forming resultant ether, such as alkyl tertiary alkyl ethers having a normal boiling point in the range of 130° F. -200° F., and particularly MTBE, while inhibiting the reaction of dialkyl sulfides present in the hydrocarbon stream with the catalyst material whereby the deactivation of the catalyst material due to the reaction of the dialkyl sulfides with the catalytic material is substantially reduced or avoided.

Therefore, the present invention is directed to any catalytic reaction process, but preferably to catalytic distillation reaction processes, performed in a manner which minimizes or substantially avoids the reaction of dialkyl sulfides and the catalytic material, which has been discovered to be responsible for deactivation of acidic catalysts used in the catalytic distillation reaction zone.

In one embodiment, the dialkyl sulfides present in the hydrocarbon stream may be removed by subjecting the streams to an adsorption treatment before introducing the stream into the catalytic reaction zone. Preferably the adsorption of the dialkyl sulfides is performed in a cyclic operation involving the use of two adsorption columns.

In another embodiment, the catalytic reaction is performed by introducing sufficient amounts of oxygenates to the reaction zone to inhibit the reaction of the dialkyl sulfides present in the feed with the catalyst material. In accordance with the present invention, the oxygenates suitable for this purpose are preferably oxygen-containing hydrocarbons, such as those selected from the group consisting of ethers, alcohols and mixtures thereof, preferably, wherein the ethers are selected from the group consisting of methyl sec-butyl ether, methyl n-butyl ether, and tert-amyl methyl ether (TAME), and most preferably TAME, and wherein the alcohol is selected from the group consisting of $C_3$ alcohols, $C_4$ alcohols, $C_5$ alcohols, ethanol and methanol, with methanol being preferred.

In yet another embodiment, both of the previously described embodiments may be used in the same catalytic reaction process. In such case, the hydrocarbon stream is subjected to an adsorption technique to remove dialkyl sulfides from the stream prior to adding oxygenates into the stream for introduction into the catalytic reaction zone.

The dialkyl sulfide found in hydrocarbon streams which has been discovered to be the most responsible for deactivation of the catalyst is dimethyl sulfide.

For purposes of producing methyl tertiary butyl ether (MTBE), the preferred components of the feed comprise isobutene and methanol.

Catalysts which have been found to be suitable for use in this process of the present invention include cat- ion exchange resins. Preferred catalysts for purposes of performing catalytic distillation processes in accordance with the present invention, however, are acid catalysts, such as acidic resin catalysts. A more preferred catalyst for purposes of the present invention is a macroreticular sulfonic acid cation exchange resin, with a member selected from the group consisting of Amberlyst 15, Lewatit SPC 118 BG (manufactured by Mobay/Bayer), Dowex M-31 and Dowex DR-2040 (manufactured by Dow Chemical Company) being more preferred, with Dowex DR-2040 being most preferred.

In a typical hydrocarbon stream subjected to a catalytic reaction process, i.e., one which has not been subjected to a treatment effective to reduce or substantially eliminate dialkyl sulfides from the stream in accordance with one embodiment of the present invention, dimethyl sulfide may be present in an amount up to about 4 wt %, and more typically in an amount within the range of up to about 10 ppm-50ppm. In such case the oxygenate, such as methanol, is present in the catalyst zone in an amount of at least about 4% by weight of said hydrocarbon stream and preferably 4% to 7% in the liquid phase in the region of the distillation tower containing the catalyst.

BRIEF DESCRIPTION OF THE DRAWING

The Figures annexed hereto are flow diagrams showing catalytic distillation processes in accordance with the present invention.

DETAILED DESCRIPTION

Figure 1:
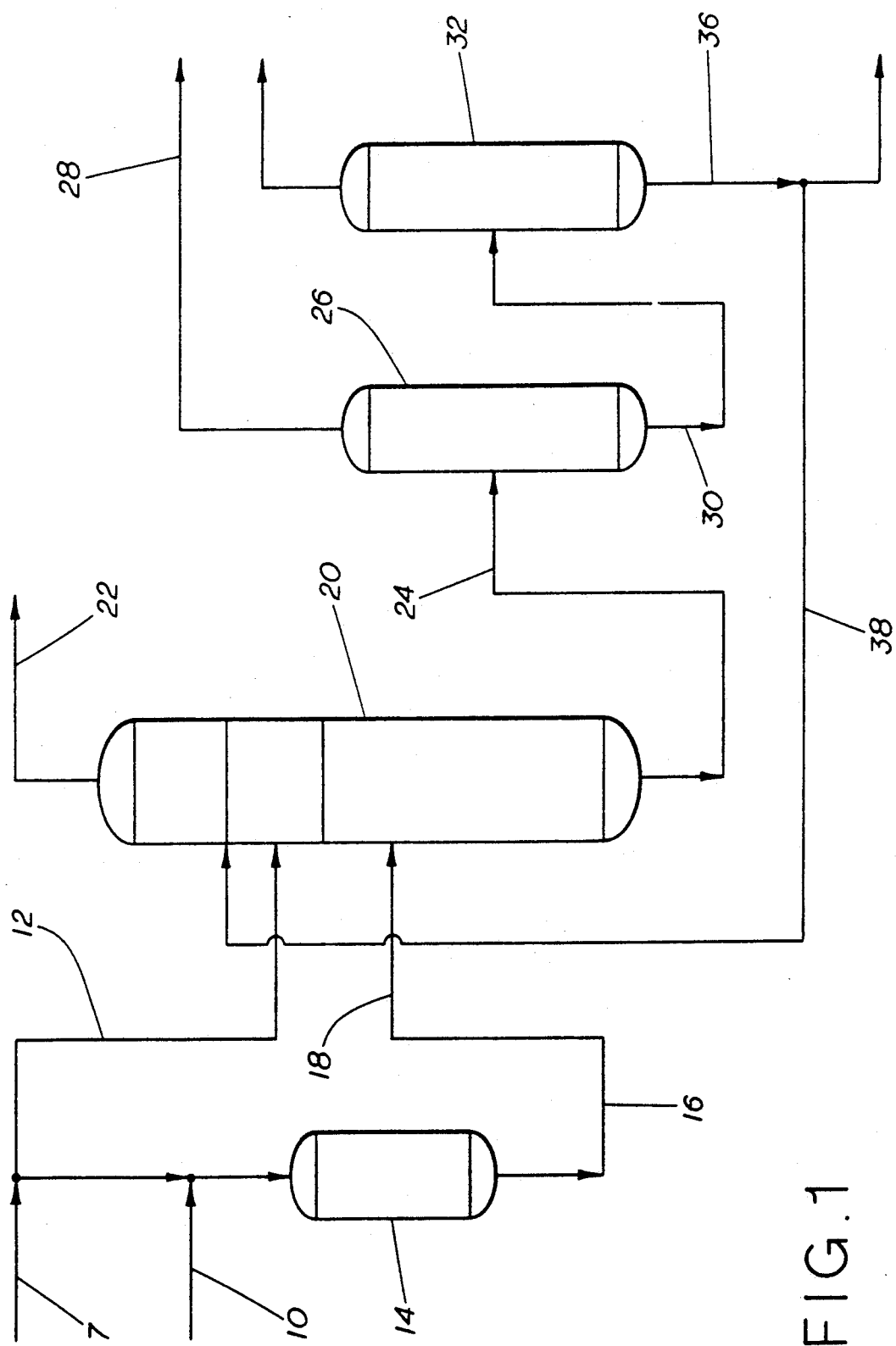
FIG. 1 is a flow diagram of a catalytic distillation process wherein oxygenates are introduced into the distillation column.

The present invention is based on the discovery that typical hydrocarbon streams which are subjected to catalytic reaction processes in the producing of ether, such as alkyl tertiary alkyl ethers, and particularly such ethers having a normal boiling point within the range of 130° F-200° F., and most notably MTBE, contain dialkyl sulfides, such as dimethyl sulfide (DMS), which react in the presence of the acidic sites on the catalyst material so as to result in the neutralization of these sites with the concomitant loss of catalyst activity. This has been found to be particularly the case for the production of MTBE by catalytic distillation reaction processes. Thus, the present invention relates to performing catalytic reactions in a manner which minimizes or substantially avoids reaction of dialkyl sulfides, and particularly dimethyl sulfide, which may be present in the hydrocarbon stream when fed or introduced into the catalytic reaction zone, such as a catalytic distillation column, even though the hydrocarbon stream may have previously been subjected to procedures in an attempt to remove contaminants, such as cationic material, therefrom which were believed to be responsible for deactivation of catalysts.

Accordingly, the present invention is directed to any catalytic reaction process, but preferably to catalytic distillation reaction processes, which are performed in a manner which minimizes or substantially avoids the reaction of dialkyl sulfides in the presence of the catalytic material which has been discovered to be responsible for deactivation of acidic catalysts used in the catalytic distillation reaction zone.

In general, therefore, the present invention is directed to any process whereby a reaction of dialkyl sulfides and catalyst material is minimized or substantially avoided.

One embodiment of the present invention, relates to catalytic reaction processes of hydrocarbon streams containing dialkyl sulfides, and particularly catalytic reactions of isoolefins, such as isobutene, containing dimethyl sulfide, over an acid catalyst, such as an acid resin catalyst. In this embodiment, the deactivation of the catalyst material used in such catalytic reaction processes is minimized or substantially eliminated by introducing oxygenates in addition to the hydrocarbon stream into the catalytic reaction zone.

In another embodiment of the present invention, which may also be referred to herein as dimethyl sulfide adsorption, a hydrocarbon stream essentially devoid of dialkyl sulfides, such as dimethyl sulfide, is provided for example by removing, and preferably substantially eliminating all, dialkyl sulfide from the hydrocarbon stream prior to contacting the hydrocarbon stream with the acidic catalyst material in the catalytic reaction zone, preferably in the distillation column used in a catalytic distillation reaction process.

An embodiment related to the previously mentioned embodiments is a catalytic reaction process which involves reducing or substantially eliminating dialkyl sulfides, and preferably dimethyl sulfide, from the hydrocarbon stream, preferably by an adsorption technique, prior to the stage in the process where the hydrocarbon stream and oxygenates, such as methanol, are introduced into the catalytic reaction zone.

Another embodiment contemplated for purposes of the present invention is to provide a catalyst appropriate for the reaction of choice for the production of alkyl tertiary alkyl ethers, such as those having a normal boiling point in the range of 130° F.-200° F., e.g. MTBE, which is essentially non-susceptible to reaction with the dialkyl sulfides, such as dimethyl sulfide, present in the hydrocarbon feed.

Although the detailed description of the present invention including the preferred and best mode is specific to the production of methyl tertiary butyl ether wherein the hydrocarbon stream comprises isobutene and methanol, it should be understood that the present invention is also applicable to the production of other alkyl tertiary alkyl ethers, and particularly those having a normal boiling point falling within the range 130° F.-200° F., wherein the isoolefins and alcohols used would be selected from the groups of isoolefins and alcohols suitable for the reaction of choice in the production of the desired alkyl tertiary alkyl ether. For example in the case of the production of tertiary amyl methyl ether (TAME), the isoolefin may be an isoamylene such as either or both of 2-methy-butene-1 and 2-methy butene-2, and the alcohol is methanol. Ethanol, however, would be the alcohol used to produce tertiary amyl ethyl ether and ethyl tertiary butyl ether. Suitable alcohols useful for purposes of the present invention, therefore, include $C_3$ alcohols, $C_4$ alcohols, $C_5$ alcohols and ethanol in addition to methanol.

The Oxygenate Procedure

This method of the present invention involves feeding a mixture containing isobutene and dimethyl sulfide into a feed zone of a reactor, feeding methanol and/or other oxygenates into the feed zone, and contacting the resultant mixture of isobutene, dimethyl sulfide, and methanol with a fixed bed acidic cation exchange resin in the reaction zone thereby catalytically reacting the isobutene with the methanol under conditions which favor forming resultant MTBE while inhibiting reaction of the dimethyl sulfide with the catalyst material so as to substantially minimize or avoid deactivation of the catalyst material.

A critical parameter in the manufacture of MTBE is the maintenance of high catalytic activity. In the synthesis of MTBE, as practiced in the art, however, catalyst deactivation has been shown to occur by different mechanisms in different areas of the process. For example, in the fixed bed or tubular reactor, wherein an acidic resin, such as Amberlyst 15 (trademark), is employed to catalyze the formation of MTBE from isobutene and methanol, deactivation of the catalyst occurs over time if the catalyst is exposed to cationic or strongly basic material, such as metals, nitrogen compounds, and the like. In order to drive the reaction of methanol and isobutene to MTBE to completion, however, it has been proposed to use the same acidic resin catalyst downstream of a first stage reactor, thereby permitting more complete utilization of the isobutene in the feed.

Due to the relatively low concentration of oxygenates, such as methanol, in the downstream portion of the system, however, the catalyst has a tendency to deactivate over time even in the absence of cationic material. Prior to the discovery of the present invention, i.e., that this deactivation results from the reaction of low levels, i.e., as low as 10 ppm or lower, of dimethyl sulfide with highly acidic catalyst sites which are present primarily due to the relatively low levels of methanol, i.e., about 0.6-2 wt. %, and MTBE in the reaction zone, it is not believed that those skilled in the art had identified the cause of the problem, much less taught or suggested the solution for the problem which is the crux of the present invention as described in more detail hereinbelow.

One embodiment of the present invention, therefore, is the discovery that increasing the levels of oxygenates, i.e., methanol or other alcohols as well as ethers, attenuates the acidity of the catalyst so that reaction between dimethyl sulfide and catalyst is substantially reduced without adversely affecting the reaction of choice, i.e., the reaction of alcohol and isobutene to MTBE.

Where oxygenates, such as methanol, are introduced into the reaction zone, the catalyst material may be any material appropriate for the reaction, such as an acid catalyst, such as catalytic metals and their oxides or halides suitable for a multitude of catalytic reactions and particularly heterogeneous with the reaction or other fluids in the system. The term "catalyst" or "catalytic material", therefore, as used herein includes any solid material which is recognized for the reaction under consideration as performing as a catalyst.

For example, where the present invention is practiced in a catalytic distillation process, the catalytic material may be in any form which permits its incorporation into a distillation tower, such as a fixed bed, but may also be in a form which serves as a distillation packing, for example, rings, saddles, balls, irregular pieces, sheets, tubes, spirals, packed in bags, plated on grills or screens, and reticulated polymer foams.

Catalysts which have been found to be suitable for use in this process of the present invention include cation exchange resins. Preferred catalysts for purposes of the present invention, however, are acid catalysts, such as acidic resin catalysts. A more preferred catalyst for purposes of the present invention is a macroreticular sulfonic acid cation exchange resin, selected from the group consisting of Amberlyst 15 (trademark), Lewatit SPC 18 BG, Dowex M-31, and Dowex DR-2040, with Dowex DR-2040 being most preferred.

In accordance this embodiment of the present invention, it has been found that deactivation of the acidic resin catalyst can be substantially reduced by maintaining the methanol concentration in the liquid phase in the catalyst reaction zone preferably at about 4 wt. % or higher. As an alternative, catalyst deactivation can be substantially reduced by injecting or recycling oxygenates, such as any suitable oxygen-containing hydrocarbon, e.g., alcohols or ethers, into the catalyst zone at concentrations appropriate for the particular oxygenate. For example, compounds which normally co-exist in the feedstreams from which isobutene is normally reacted, but in low concentrations, are suitable for this purpose. These include, but are not limited to, methyl sec-butyl ether, methyl n-butyl ether, tert-butyl alcohol, $C_3$ alcohols, $C_5$ alcohols, ethanol, methanol, methyl tert butyl ether (MTBE), and tert-amyl methyl ether (TAME). Of these, TAME is preferred in that it imparts several distinct advantages because its presence does not impede the formation of MTBE and because it is easily separable from the reaction products and recycled.

EXAMPLE I

The following tests were conducted as evidence that dimethyl sulfide, and not other sulfur-containing compounds, is a poison for Amberlyst-15 (trademark) acid catalyst under conditions used commercially in the production of MTBE.

The reactions were carried out in a laboratory-scale, continuous-flow tubular reactor. The acid catalyst resin, generally 10 cc, was placed in a metal tube and held in place by glass wool plugs. The tube was jacketed by a larger tube with circulating hot water to control the temperature of the reaction, which was generally held at 70° C. The single liquid feed was introduced by a metering pump controlling the flow of the liquid to yield a Liquid Hourly Space Velocity (LHSV) of 4. The back pressure at the exit of the reactor, 180 psig, was kept high enough so that the reactor was filled by liquid, with no vapor. The acid catalyst used for purposes of this test was Amberlyst-15 (trademark), obtained as a fresh sample from a commercial plant. The feed to the laboratory reactor was also obtained from a commercial plant, and was composed of 2.67 wt. % isobutylene, and more than enough methanol to react with the isobutylene to yield in MTBE, with the balance of the feed being essentially mixed butenes and butanes. The progress of the reaction was monitored by taking small liquid samples under pressure from the reactor exit and analyzing them on a capillary gas chromatograph. The conversion of isobutylene was then calculated and was used to monitor the activity of the catalyst.

For purposes of this comparison, the following tests were run:

TABLE I

| Run | Feed Additive | Observations |
|---|---|---|
| IA | no additive | Isobutylene conversion remained constant at 90% for 16 hours. |

TABLE I-continued

| Run | Feed Additive | Observations |
|---|---|---|
| IB | 5.6 wt. % Dimethyl Sulfide | The isobutylene conversion declined steadily from 90% to less than 50% over 19 hours. The spent catalyst in this reaction analyzed for an acidity of 2.8 milliequivalents per gram, down from the normal 4.5 meq/g in fresh catalyst. |
| IC | 5.6 wt. % Ethyl mercaptan | The isobutylene conversion remained constant at 90% for 11 hours; this was followed by straight feed for 18 hours, with isobutylene conversion again remaining constant at 90%. |
| ID | 2.9 wt. % Dimethyl sulfide 3.0 wt. % Ethyl mercaptan | The isobutylene conversion declined steadily over 18 hours at half the rate as when 5.6 wt. % dimethyl sulfide was added, for example in Run IB. |
| IE | 7.3 wt. % Methyl t-butyl sulfide | The isobutylene conversion remained constant at 88% for 17 hours, followed by straight feed for 7 hours, with the isobutylene conversion remaining constant at 89%. |

The foregoing comparison demonstrates that under these conditions, dimethyl sulfide is a poison for the acid catalyst used to produce MTBE from isobutylene and methanol, and that the tendency of dimethyl sulfide to poison the catalyst is not affected by the presence of other sulfurcontaining compounds, such as mercaptan, e.g., ethyl mercaptan, nor is the catalyst poisoned by other organosulfur compounds, such as ethyl mercaptan or methyl tertiary-butyl sulfide.

EXAMPLE II

The following comparison demonstrates the effect of the methanol content of the feed on the dimethyl sulfide poisoning of the catalyst. The run conditions used were substantially the same as those used in the previous Example. For purposes of this Example, the feed had an initial methanol content of about 3 wt. % and an isobutylene content of about 3.2 wt. %. For Runs IIA and IIB the methanol concentration was adjusted to 4%. In Run IIA, 0.5 wt. % dimethyl sulfide was introduced into the feed; and for Run IIB, 2 wt. % dimethyl sulfide was included in the feed. In Run IIC, 5 wt. % dimethyl sulfide was included in the feed and an additional 3 wt. % methanol for a total of 6 wt. % methanol was included in the feed. In Run IID, the methanol content of the feed was 1.5 wt. % and isobutylene content was 2.5 wt. %; and 5 wt. % of dimethyl sulfide was added to the feed.

The results of the observations are tabulated below:

TABLE II

| Run | Dimethyl Sulfide wt. % | Methanol wt. % | Observations |
|---|---|---|---|
| IIA | 0.5 | 4.0 | The conversion remained at 85–90% and the performance of the catalyst was not affected over a period of a 15 to 18 hour run. |
| IIB | 2.0 | 4.0 | The conversion remained at 85–90%, and the performance of the catalyst was not affected over a period of a 15 to 18 hour run. |
| IIC | 5.0 | 6.0 | Very little effect |

TABLE II-continued

| Run | Dimethyl Sulfide wt. % | Methanol wt. % | Observations |
|---|---|---|---|
| | | | manifested by a drop to about 75% conversion after 15 hours of the run. |
| IID | 5.0 | 1.5 | Resulted in poisoning of the catalyst in a period of 8 to 12 hours of the run during which the conversion dropped to less than 50%. |

The foregoing comparison demonstrates that feeds containing about 4 wt. % methanol spiked with 0.5 to 2 wt. % dimethyl sulfide do not poison the catalyst over a run period of 15 to 18 hours. Similarly, feeds containing about 6 wt. % methanol spiked with 5 wt. % dimethyl sulfide appear to experience a small reduction of the conversion after 15 hours of a run. In contrast, a feed containing about 1.5 wt. % methanol and 5 wt. % dimethyl sulfide, however, poisons the catalyst within 8 to 12 hours of the run.

Referring now to FIG. 1, a schematic system is shown, which can be used to produce MTBE.

A feed stream 7 containing a stoichiometric amount of methanol based on isobutylene is introduced together with an isobutylene containing feed stream 10 to a lead synthesis reactor 14. The lead synthesis reactor 14 is provided with an acidic resin catalyst, such as Amberlyst-15 (trademark), Dowex DR-2040, Lewatit SPC 18 BG, or Dowex M-31, and is heated to an appropriate temperature. The effluent or product stream 16 leaving the reactor is composed of MTBE, unreacted hydrocarbons and methanol (MeOH). The resultant product stream is the feedstream 18 which is then fed to a distillation column 20. The vaporized overhead 22 is composed of raffinate depleted in olefins branched at the point of unsaturation (sometimes referred to as tertiary olefins) which is passed through methanol removal and final clean-up procedures. In accordance with the present invention, however, a stream 12 of methanol is introduced into the catalytic distillation reaction zone, wherein the catalyst may also be Amberlyst 15 or equivalent but is preferably Dowex DR-2040. The effluent is then passed to a product topping tower 26 wherein C5 hydrocarbons are removed for separate processing. The resultant effluent stream 30 is then passed to product tailing tower wherein MTBE is removed as product. The effluent 36 from tailing tower contains various components including oxygenates, such as TAME, which are recycled through conduit 38 to supply oxygenate the catalyst reaction zone.

A catalytic reaction process which is particularly amenable to being practiced in accordance with the present invention may be a catalytic distillation process performed in a conventional manner, such as that which is disclosed by any of the previously discussed U.S. Patents in the name of SMITH, Jr., the disclosure of which are hereby specifically incorporated by reference thereto.

EXAMPLE III

A feed stream 10 containing 13 wt. % isobutylene, 30 wt. % isobutane, 14 wt. % butene-1, 13 wt. % n-butane, 18% 2butenes, 0.5 wt. % butadiene, 6% isopentane, approximately 5 wt. % other C5 hydrocarbons (including paraffins, olefins, and diolefins, 200 wt.ppm methane thiol and 10 wt.ppm dimethyl sulfide is combined with a methanol stream 7 in the weight ratio of methanol in stream 7 to isobutylene in stream 10 of 0.75:1.0. This combined stream is heated to 130° F. to 170° F. and introduced to a lead synthesis reactor which contains acidic ion exchange resin catalyst such as Amberlyst 15 (trademark) in a quantity which provides for a weight space velocity of 3.5 W/H/W to 4.0 W/H/W.

In passing through the lead synthesis reactor 14, approximately 85 wt. % of the isobutylene in the feed stream is converted to MTBE. Also, in this reactor, all strongly basic compounds and metallic compounds contained in the hydrocarbon or methanol feed react with acidic catalyst and are removed from the feed. In so reacting with the catalyst, these basic compounds reduce the number of acidic sites on the catalyst and, over time, result in its deactivation.

The hydrocarbon stream 16 which exits reactor 14 contains 17 wt. % MTBE, about 2 wt. % isobutylene and all the remainder of unreacted hydrocarbon and methanol. This stream is fed to a catalytic distillation tower 20. The overhead from this column containing only 0.5 wt. % isobutylene in hydrocarbons is passed through methanol removal and sent to other processing.

In this embodiment of the present invention, additional methanol stream 12 is introduced into the catalytic distillation reaction zone at a rate sufficient to result in the liquid stream passing through the catalyst zone containing 4 wt. % MeOH or higher-, and preferably 6-7 wt. %. This may be accomplished by introducing sufficient amounts of stream 12 such that the ability of overhead stream 22 to form an azeotrope with MeOH is exceeded which results in MeOH being concentrated in the liquid phase in the catalyst zone of the distillation tower. However, without the addition of stream 12, the catalyst placed in the distillation tower would react with dimethyl sulfide in the feed hydrocarbon stream to rapidly deactivate. Thus, the inclusion of additional MeOH in the concentrations mentioned greatly reduces the rate of this deactivating mechanism resulting in a much improved catalyst life.

The bottoms stream 24 from the distillation tower contains 25 wt. % MTBE and 2% TAME in admixture with other hydrocarbons and alcohols boiling higher than n-butenes. This stream 24 is passed to a topping tower 26 wherein C5 hydrocarbons lighter than MTBE are removed for further processing. The resultant bottoms stream 30 is passed to a product tailing tower wherein MTBE is removed as overhead product. The bottoms stream 36 from the tailing tower contains approximately 75 wt. % TAME and various other hydrocarbons and oxygenates, part of which can be recycled to the catalyst reaction zone through conduit 38 to supply additional oxygenates without substantially affecting the equilibrium of the isobutylene plus methanol yielding MTBE reaction.

Thus, the method in accordance with the present invention involves inventive procedures for avoiding the principal deactivating mechanism through the use of increased concentrations of oxygenates in the reacting zone.

Dimethyl Sulfide Adsorption

In accordance with the present invention, an alternative procedure has been developed to minimize or substantially eliminate the deleterious effects which would otherwise be caused by the presence of dimethyl sulfide in the catalytic reaction zone. This procedure is preferably used in lieu of the previously described procedure which involves the introduction of oxygenates into the catalytic reaction zone, but may be used in conjunction with the introduction of oxygenates to better ensure that the catalytic material is not subject to a reaction with dimethyl sulfide.

Figure 2:
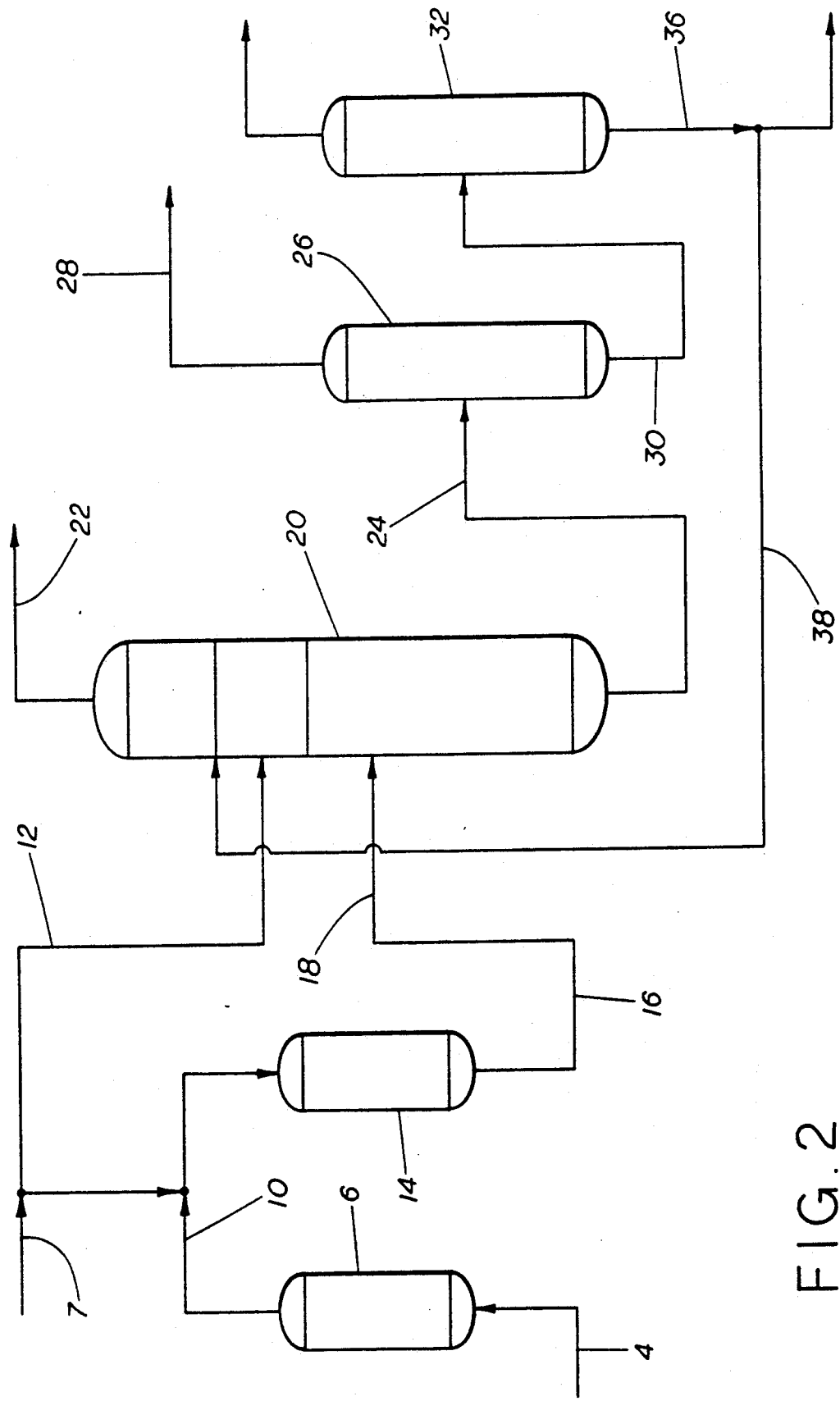
FIG. 2 shows a substantially identical flow diagram as in FIG. 1 except an adsorption column is installed prior to the mixing point of the hydrocarbon stream feed and the methanol streams.

In this procedure, the sulfide contaminants in the hydrocarbon stream may be removed by installing an adsorption column prior to the mixing point of feed 4 and methanol 7 streams in a catalytic distillation procedure otherwise the same as discussed above with respect to FIG. 1. The removal has been discovered to be most effective for a methanol-free feed stream. This arrangement is illustrated in the FIG. 2. In practice, the removal is preferably accomplished with a cyclic operation involving the use of two adsorption columns so that while one column is adsorbing the sulfides, the other column is being regenerated to recover the capacity.

The adsorbents suitable for removing dialkyl sulfides for purposes of the present invention include crystalline aluminosilicates, such as zeolite X, zeolite Y, zeolite Beta, silicalite, mordenite, and metal oxides, such as cobalt oxide, chromium oxide, nickel oxide and molybdenum oxide, supported on alumina and carbon.

EXAMPLE IV

The following tests were conducted as evidence that the previously identified adsorbents could remove dialkyl sulfides from an ether synthesis hydrocarbon stream.

The dynamic experiments were carried out in a laboratory-scale, continuous-flow tubular reactor. The adsorbent, generally 5 cc, was placed in a metal tube and held in place by porous metal plugs. The tube was kept at ambient temperature. The single liquid feed was introduced by an HPLC pump controlling the liquid flow to yield a Liquid Hourly Space Velocity of 4. The back pressure at the exit of the tube was kept at 300 psig. The adsorbent chosen for this dynamic test was sodium-X zeolite. The feed was a synthetic blend of butene-1, isobutylene, dimethyl sulfide, ethyl mercaptan, and n-heptane. The progress of the adsorption was monitored by taking small liquid samples from the tube exit and analyzing them on a capillary gas chromatograph for dimethyl sulfide and ethyl mercaptan concentrations. The dynamic study results are summarized in the following table.

TABLE III

| Run | Feed Composition | Observations |
| --- | --- | --- |
| I | 110 ppm DMS in n-heptane | DMS concentration remained below 1 ppm for 72 hours |
| II | 110 ppm DMS in 5% butene-1, 7% isobutylene, and 88% n-heptane | DMS concentration remained below 1 ppm for 72 hours. |
| III | 30 ppm DMS and 110 ppm ethyl mercaptan in 5% butene-1, 7% isobutylene and 88% n-heptane | DMS concentration remained below 1 ppm for 50 hours. |
| IV | The same as in Run III | The Na-X zeolite used in Run III was regenerated with a hot nitrogen purge at 350–400° F. The regenerated adsorbent showed the same DMS removal as in Run III. |
| V-XII | The same as in Run III | 8 cycles of regeneration were conducted. In each cycle the DMS concentration in product was below 1 ppm for 50 hours. |

Related to this, sulfur components in a feed stream have historically presented a problem because of their tendency to deactivate catalysts. Mercaptans can usually be removed by a caustic wash, but this method has not been found to be effective in removing sulfides, such as dialkyl sulfides.

Therefore, it was unexpectedly discovered that metal oxides on various supports can be effective in removing both mercaptans and sulfides. For this purpose metal oxides such as $MoO_3$, $NiO$, $Cr_2O_3$, and $CoO$ and their mixtures have been screened on supports such as alumina and carbon, and were found to be effective to various degrees in reducing the concentration of mercaptans and sulfides present in an olefinic/hydrocarbon streams at room temperature.

EXAMPLE V

Static tests were carried out on a group of metal oxides to determine their capability for removing sulfur compounds from a hydrocarbon refinery stream.

These hydrocarbon streams were screened at ambient temperature using a synthetically blended feed of ethyl mercaptan, dimethylsulfide and butene-1 in heptane Samples were removed for gas chromatographic analysis after 24 hours. Results are listed in the table below.

| Feed Composition: | 90.1% n-heptane |
| --- | --- |
|  | 9.0 butene-1 |
|  | 43 ppm dimethylsulfide |
|  | 104 ppm ethylmercaptan |

| Metal Oxide | Product Sulfur Level |
| --- | --- |
| $NiO/MoO_3$/Alumina | <1 ppm Sulfur |
| $CoO/MoO_3$/Alumina | <1 ppm Sulfur |
| $MoO_3$/Carbon | <1 ppm Sulfur |
| $Cr_2O_3$/Alumina | no Sulfur |

Thus, not only is the present invention based on the discovery that the presence of dialkyl sulfides in the hydrocarbon stream exposed to the catalyst is responsible for deactivation of the catalyst material, but is also directed to an unexpected procedure for removing this particular sulfur contaminant from the hydrocarbon stream.

EXAMPLE VI

The following tests were conducted to substantiate the previous findings that the presence of dimethyl sulfide reacts with the catalyst so as to cause the catalyst to become deactivated during the preparation of MTBE from isobutylene and methanol over Amberlyst-15 (trademark).

Samples of deactivated catalysts were removed from three locations in a synthesis tower used in the commercial preparation of MTBE for isobutylene and methanol. Each of these samples, along with a sample of fresh unused catalyst, was analyzed on a cross-polarization magic angle spinning (CPMAS) carbon 13 nuclear magnetic resonance ($C^{13}NMR$) instrument.

All three deactivated samples exhibited a sharp peak at 27 ppm, whereas the fresh catalyst did not exhibit such a peak. In this regard, the literature reports a range of 27.5–28.1 ppm for the $C^{13}NMR$ of the trimethylsulfonium ion.

To further substantiate the indication that the reaction of dimethyl sulfide with the catalyst causes a deactivation of same, one of the samples of used catalyst was reacted with 10% DCl in $D_2O$ and the resultant solution was used for proton NMR and $C^{13}NMR$ If the trimethyl sulfonium cation were present it would be expected to be hydrolyzed and the resultant solution should exhibit peaks for this cation. The proton NMR showed a peak at 3.13 ppm. The $C^{13}$ NMR gave only one peak at 27.17 ppm. In each instance, these peaks were found as expected.

Finally, fresh catalyst, i.e., Amberlyst-15 (trademark), was reacted with a solution of trimethylsulfonium iodide in water/methanol at room temperature. The resultant solid was carefully washed free of any excess reactants and dried at 100° C. in vacuum. The NMR of this material now exhibited the same peak as the used catalyst.

The foregoing findings substantiate the discovery of the present invention, i.e., that dimethyl sulfide reacts with the catalyst thereby depositing trimethylsulfonium cations on the catalyst during catalytic reactions of feedstreams and the preparation of MTBE from isobutylene and methanol over Amberlyst-15 (trademark) catalyst.

In general, therefore, it can be said that the present invention may be used in connection with any reaction of a hydrocarbon stream over an acid catalyst, such as Amberlyst-15 or Dowex DR-2040. Included among the catalytic reactions to which the discoveries of the present invention are particularly suitable are catalytic isomerization, esterification, dimerization, cracking and distillation processes, although all other types of reactions are contemplated within the scope of the invention process, for example, chlorination, hydration, dehydrohalogenation, alkylation, polymerization and the like.

For example, isomerization reactions which are catalyzed by an acidic on exchange resin catalyst have been found to deactivate if a feedstream containing dialkyl sulfides, such as dimethyl sulfide, is passed over the catalyst. Although in the past it was previously thought to include alcohols and water at this stage of catalytic isomerization reaction to provide the necessary environment to render the catalyst operable, it has been found that alcohols tend to react with the isoolefins to form ethers thereby resulting in a product loss. Moreover, the presence of water causes solubility problems and also tends to react with the isoolefins to form alcohol; thus, water is not a particularly desirable solvent. Water also deactivates the catalyst. It has also been proposed to include ether with isoolefins to provide the necessary environment for resin catalyst operability, with tertiary amyl methyl ether (TAME) and methyl tertiary butyl ether (MTBE) being preferred, and TAME being most preferred, for this purpose.

Prior to the present invention, however, the art did not recognize that dialkyl sulfides, such as dimethyl sulfide, present in the feed contributed to the deactivation of the catalyst, much less recognize that removing dialkyl sulfide from the hydrocarbon stream would reduce catalyst deactivation, nor that including oxygenates with the isoolefins in accordance with the present invention would substantially inhibit deactivation of the catalyst.

Therefore, it is believed that in general isomerization reactions over acidic ion exchange resin catalysts can be improved and deactivation of the catalyst minimized by removing dialkyl sulfides from the hydrocarbon stream or by the presence of an oxygenate, such as alcohols and ethers. Accordingly, the principles of the present invention may be applied to the isomerization of numerous hydrocarbon feed compositions, such as feedstreams containing a mixture of saturated hydrocarbons, other straight chain and branched olefins, and small amounts of certain diolefins. One example of such a feed is the naphtha fraction from a refinery catalytic cracking unit. In accordance with the present invention, therefore, even feedstreams containing high levels of diolefins, and even low-levels in the case of cyclopentadiene, have been found not to foul the cation exchange resin, reducing its activity, and therefore its ability to catalyze the isomerization reaction if oxygenates, such as ethers and alcohols, are included in the feed.

Although the invention has been described with reference to particular means, materials, and embodiments, from the foregoing description, one skilled in the art can easily ascertain the essential characteristics of the present invention, and various changes and modifications may be made to various usages and conditions, without departing from the spirit and scope of the invention as described in the claims that follow.

We claim:

1. A method for producing alkyl tertiary alkyl ether comprising:
    (a) supplying a feedstream comprising an isoolefin, an alcohol, and a dialkyl sulfide to a reactor;
    (b) catalytically reacting said feedstream in said reactor containing an acid resin catalyst under reaction conditions which favor forming resultant ether and producing a reactor effluent stream comprising said resultant ether, unreacted isoolefin and alcohol;
    (c) feeding said reactor effluent stream into a distillation column having a catalytic distillation reaction zone including an acid resin catalyst to separate said resultant ether from said unreacted isoolefin and alcohol; and
    (d) providing at least 45 by weight of said reactor effluent stream in said catalytic distillation reaction zone of oxygenates selected from the group consisting of ethers, alcohols, and mixtures of ethers and alcohols to inhibit a reaction of dialkyl sulfide with said acid resin catalyst in said catalytic distillation reaction zone.

2. The method as defined by claim 1, wherein said dialkyl sulfide is present in an amount up to about 4 wt. % in said reactor effluent stream in said catalytic distillation reaction zone.

3. The method as defined by claim 2, wherein said dialkyl sulfide is present in an amount up to about 50 ppm in said reactor effluent stream in said catalytic distillation reaction zone.

4. The method as defined by claim 3, wherein said dialkyl sulfide is present in an amount up to 10 ppm in said reactor effluent stream in said catalytic distillation reaction zone.

5. The method as defined by claim 1, wherein said alcohol is methanol, and said resultant ether is methyl tertiary butyl ether.

6. The method as defined by claim 1, wherein said isoolefin is selected from the group consisting of isobutylene and isoamylene.

7. The method as defined by claim 6, wherein said alcohol is selected from the group consisting of methanol and ethanol.

8. The method as defined by claim 7, wherein said resultant ether is selected from the group consisting of methyl tertiary butyl ether, ethyl tertiary butyl ether, tertiary amyl methyl ether, and tertiary amyl ethyl ether.

9. The method as defined by claim 2, wherein said acid resin catalyst in said catalytic distillation reaction zone is a cation exchange resin catalyst.

10. The method as defined by claim 9, wherein said cation exchange resin catalyst is a macroreticular sulfonic acid cation exchange resin catalyst.

11. The method as defined by claim 1, wherein said resultant ether is selected from the group consisting of methyl tert-butyl ether, and tert-amyl methyl ether.

12. The method as defined by claim 11, wherein said resultant ether is tert-amyl methyl ether.

13. The method as defined by claim 1, wherein said alcohols are selected from the group consisting of $C_3$ alcohols, $C_4$ alcohols, $C_5$ alcohols, ethanol and methanol.

14. The method as defined by claim 13, wherein said alcohol is methanol.

15. The method as defined by claim 1, wherein said dialkyl sulfide is dimethyl sulfide.

16. The method as defined by claim 15, wherein said isoolefin and said alcohol in said feedstream are isobutene and methanol, respectively, and said resultant ether is methyl tertiary butyl ether.

17. The method as defined by claim 16, wherein said methanol is present in a stoichiometric amount for reaction with said isobutene.

18. The method as defined by claim 17, wherein said dimethyl sulfide is present in an amount up to about 4 wt. % in said feedstream.

19. The method as defined by claim 18, wherein said dimethyl sulfide is present in an amount up to about 50 ppm in said feedstream.

20. The method as defined by claim 2, wherein said acid resin catalyst material in said catalytic distillation reaction zone reactor is a cation exchange resin catalyst.

21. The method as defined by claim 20, wherein said cation exchange resin catalyst in said catalytic distillation reaction zone reactor is a macroreticular sulfonic acid cation exchange resin catalyst.

22. The method as defined by claim 1, wherein said providing oxygenates comprises combining said oxygenates with said reactor effluent stream to form a mixture of oxygenates and reactor effluent stream and introducing said mixture into a feed zone of said catalytic distillation reaction zone.

23. The method as defined by claim 22, wherein said oxygenates are provided by a member selected from the group consisting of freshly supplied oxygenates, recycled oxygenates recovered as a by-product of catalytic distillation, and mixtures of freshly supplied oxygenates and recycled oxygenates.

24. The method as defined by claim 23, wherein said ether is selected from the group consisting of methyl tert-butyl ether, and tert-amyl methyl ether.

* * * * *